United States Patent [19]
Christiansen

[11] Patent Number: 4,817,423
[45] Date of Patent: Apr. 4, 1989

[54] METHOD AND APPARATUS FOR DETERMING DISTRIBUTION OF FLUIDS IN A POROUS SAMPLE

[75] Inventor: Richard L. Christiansen, Littleton, Colo.

[73] Assignee: Marathon Oil Company, Findlay, Ohio

[21] Appl. No.: 137,409

[22] Filed: Dec. 22, 1987

[51] Int. Cl.[4] ............................................. E21B 49/02
[52] U.S. Cl. ......................................... 73/153; 73/38; 73/863.21
[58] Field of Search ...................... 73/153, 38, 863.21, 73/864, 864.91; 175/20, 226; 324/376, 377

[56] References Cited

U.S. PATENT DOCUMENTS

| | | | |
|---|---|---|---|
| 2,680,833 | 6/1954 | Rothacker | 324/377 |
| 3,202,348 | 8/1965 | Strohmaier | 73/863.21 |
| 3,380,292 | 4/1968 | Le Fournier | 73/38 |
| 3,388,586 | 6/1968 | Golmard et al. | 73/38 |
| 3,683,674 | 8/1972 | Roy | 73/38 |
| 3,820,012 | 6/1974 | Molyneux | 324/377 |
| 3,859,843 | 1/1975 | Lowell | 73/38 |

Primary Examiner—Stewart J. Levy
Assistant Examiner—Kevin D. O'3 Shea
Attorney, Agent, or Firm—Jack L. Hummel; Rodney F. Brown

[57] ABSTRACT

In the process of collecting data to be used in determining the capillary pressure of immiscible fluids in a porous rock sample, fluid is expelled from the sample by spinning a sample disk about its own center axis instead of centrifuging a core plug in the usual manner. The disk is contained in a cylindrical chamber whose dimensions are only slightly larger than those of the sample disk. A rotating shaft is connected to the center of the bottom face of the chamber and vessels are connected to the chamber about its periphery to collect the expelled fluid.

11 Claims, 2 Drawing Sheets

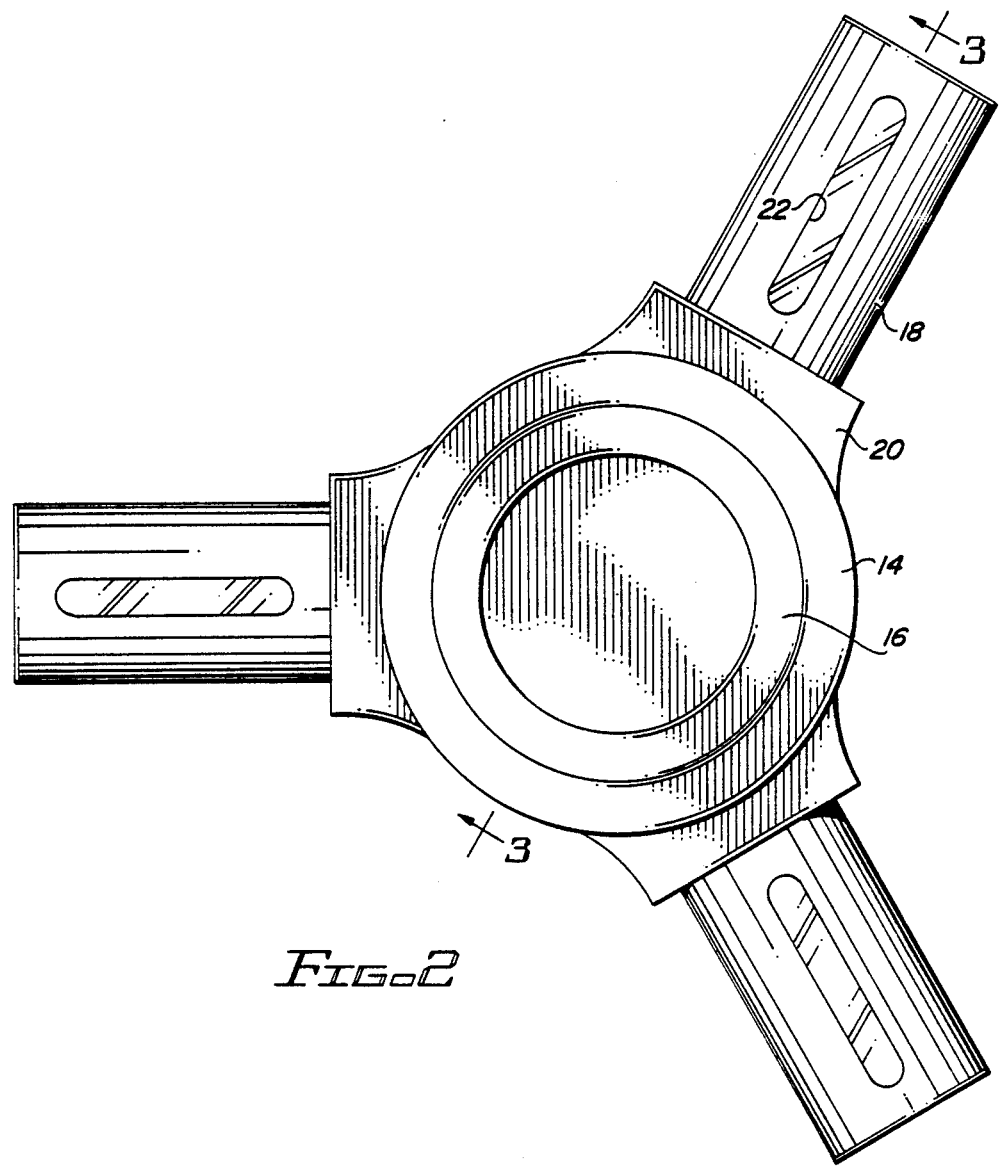
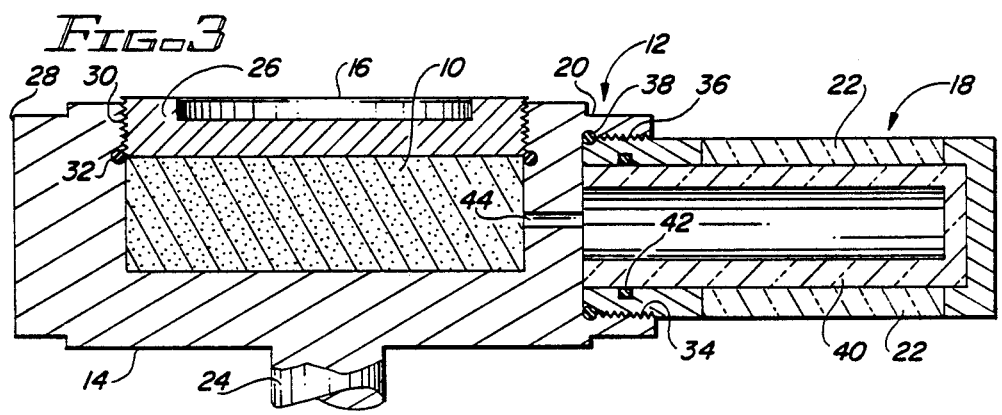

METHOD AND APPARATUS FOR DETERMING DISTRIBUTION OF FLUIDS IN A POROUS SAMPLE

FIELD OF THE INVENTION

This invention relates to a test method for use in determining the distribution of immiscible fluids in a porous medium and to apparatus for carrying out the method. More particularly, it relates to an improved method and apparatus for expelling fluid from a porous test sample in order to gather the necessary data.

BACKGROUND OF THE INVENTION

In order to determine the distribution of fluids in oil bearing rock formations from test samples it is common to saturate a core sample of the rock with one of the fluids and to submerge the sample in another fluid contained in a centrifuge chamber. Usually one of the fluids is water and the other is oil from the rock formation. The fluids are thus of different densities and are immiscible. When the centrifuge is rotated some of the fluid in the sample is expelled and is replaced in the vacated pores by the other fluid. By measuring the amount of fluid expelled at equilibrium over a series of incremental speeds the capillary pressure distribution of the sample can be mathematically determined.

Although rock samples have been tested in this manner for many years, the procedure is not without drawbacks. Traditional designs of centrifuges for these procedures are capable of handling only small rock samples. The size of rock samples has been limited by material strengths for high speed centrifuges and by restrictions in mathematical procedures for converting the results of centrifuge experiments into capillary pressure relationships. Rock samples larger than one inch in diameter and one inch in length are seldom tested. Because the rock samples are small, a number of different samples must be tested in order to get test results that can be relied upon to accurately portray conditions in the rock formation. Further, the accuracy of measurement of produced fluid volumes from small rock samples is of concern. In addition, the preferred relatively rapid mathematical differentiation of the raw data produced by the fluid expulsion tests is not always an accurate procedure for reducing raw data from core plug experiments. Without getting into details, accurate reduction of the raw data may require involved mathematical procedures depending on the dimensions of the centrifuge and the rock sample.

It would therefore be desirable to be able to test rock samples in an improved manner, in order to overcome the need to test so many samples and to enable data reduction by differentiation of the raw data.

BRIEF SUMMARY OF THE INVENTION

In order to generate the data needed to produce accurate capillary pressure curves, this invention obtains data by preparing a rock sample having an arcuate outer extremity, the curvature of which corresponds to the arc of a circle, and saturating the sample with a first fluid. The sample is then submerged in a second fluid which is immiscible with the first fluid, and is spun about an axis substantially coincident with the center of curvature of the arcuate outer extremity of the sample. The sample extends from the axis of rotation to the arcuate outer extremity thereof. Fluid expelled from the sample at any rotational speed is collected, and the set of volumes expelled at various rotational speeds is used in the calculation of the capillary pressure of the fluids in the sample.

Preferably the sample is in the form of a circular disk and is contained in a cylindrical chamber of only slightly larger dimensions. By aligning the center of the disk with the axis of a rotating shaft on which the chamber is mounted, stresses created by the large moment arm of the usual type of centrifuge are avoided, allowing the apparatus to be of a size which can accommodate relatively large disks. It is entirely possible, for example, to spin test disks measuring 6" in diameter and 2" in thickness, thereby yielding test results for a volume of rock sample equivalent to a great many separate core samples of the usual type. Furthermore, the concentricity of disk center and the axis of rotation provides for accurate and simple reduction of raw data by differentiation.

Other features and aspects of the invention, as well as its various benefits, will be ascertained from the more detailed description of the preferred embodiment of the invention which follows.

BRIEF DESCRIPTION OF THE DRAWINGS

FIG. 2 is a top view of the receptacle of FIG. 1 shown with the lid or top of the receptacle in place; and FIG. 3 is a cross-sectional view taken on line 3—3 of FIG. 2.

DESCRIPTION OF THE PREFERRED EMBODIMENT

Figure 1:
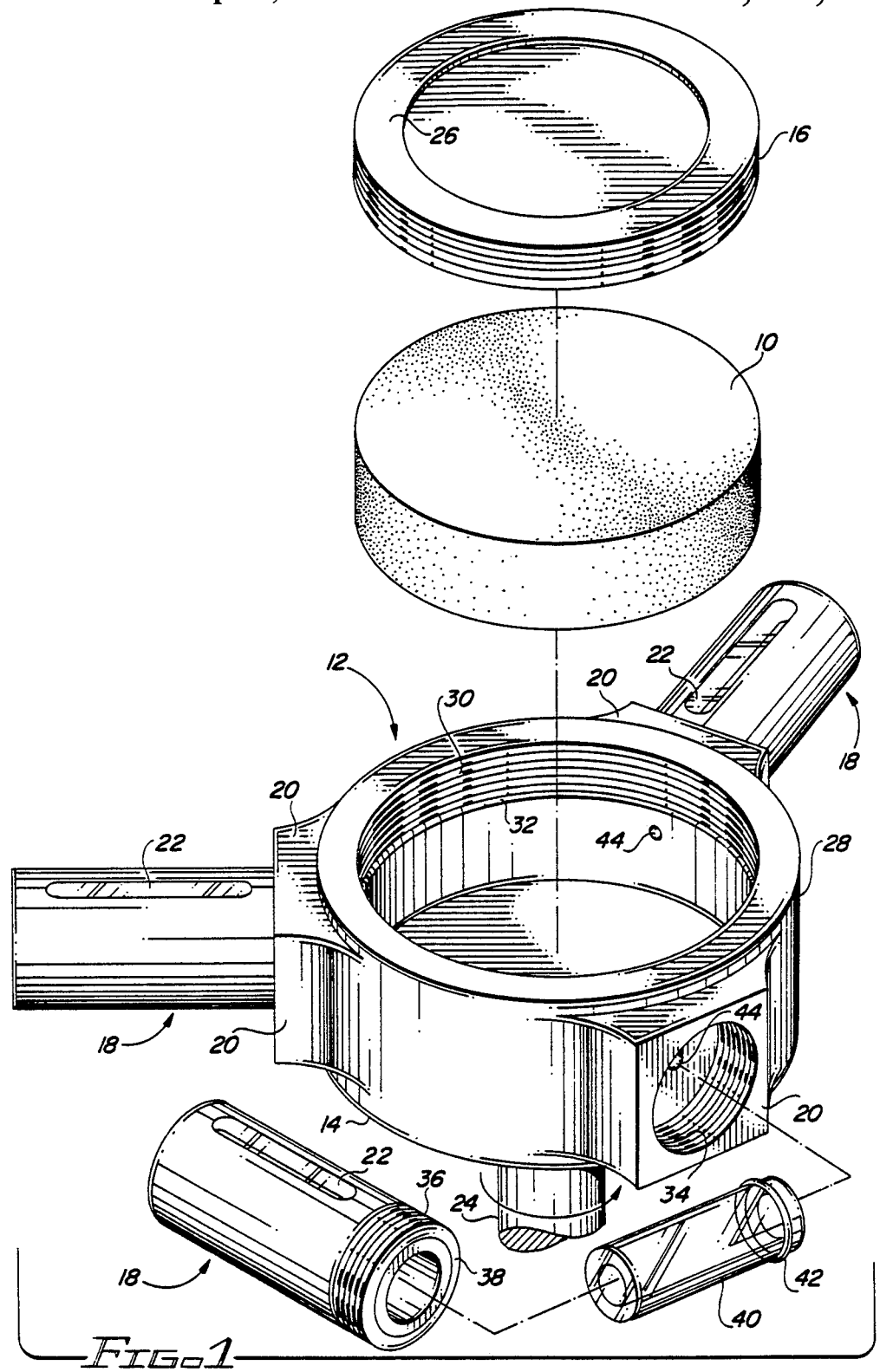
FIG. 1 is an exploded pictorial view of a receptacle for receiving a test sample disk in accordance with the present invention.

Referring to FIG. 1, the invention makes use of a sample 10 in the shape of a circular disk which fits into a cylindrical receptacle 12 comprising a bottom portion 14 and a lid 16. The diameter of the chamber formed by the interior of the receptacle is just slightly larger than the diameter of the sample disk 10. For example, if the diameter of the disk is 3.00" the diameter of the chamber may be 3.02", leaving 0.02" clearance to enable the receptacle to receive the disk. The bottom of the disk rests on the bottom wall of the receptacle and the top of the disk would be close to or touching the lid. Fluid collection chambers 18 are shown as extending outwardly from bosses or lugs 20 attached to or formed integrally with the side of the bottom portion 14 of the receptacle 12 for receiving fluid expelled from the disk during spinning. The fluid collection chambers contain windows 22 for viewing the liquid level inside the chambers.

The bottom portion 14 of the receptacle 12 is shown mounted on the upper end of a rotatable shaft 24 of a motor, not illustrated. Any suitable motor capable of providing the high rotational speeds required may be used. Speeds in the range of 5,000–20,000 RPM, for example, are normally required in order to expel fluid from a saturated sample through the range of spin rates necessary to generate data for producing a capillary pressure curve.

Three chambers 18 for receiving and collecting fluid expelled from the sample are shown as being equally spaced about the circumference of the receptacle 12. Any suitable number or arrangement of chambers 18 may be utilized, so long as they are sufficient to collect the amount of fluid expelled from the sample. The cumulative volume of the chambers 18 will be significantly larger than the volume of the tube normally used to collect fluid expelled during operation of the usual type of centrifuge. For example, while a typical amount of fluid expelled from a core plug having a diameter of 1" and a length of 1" may be in the order of 3 cc or less, the amount expelled from a disk having a diameter of 3" and a length of 1" may be as much as 20-30 cc. In general, the fluid collection chambers should be large enough to contain ¼ to ⅓ of the volume of the sample disk. In addition to the size consideration, the collecting chambers 18 should preferably be equally spaced about the periphery of the receptacle 12 in order to maintain the apparatus in balanced condition as it is spinning.

As best shown in FIGS. 1 and 3, the disk 10 can be seen to fit snugly in the chamber of the receptacle 12 formed by the space between the lid 16 and the bottom portion 14. The lid 16 has an upwardly extending side wall 26 which engages the inner surface of the upper portion of the side wall 28 of the bottom portion 14 of the receptacle. Although any desired arrangement for maintaining the lid in fluid-tight condition can be employed, for purpose of illustration the walls 26 and 28 are shown as being attached by a threaded connection 30, with an O-ring 32 being provided to function as a seal.

Still referring to FIGS. 1 and 3, the collection chamber 18 is shown as comprising an outwardly extending generally cylindrical container or nipple which is seated in a socket 34 extending through the associated boss 20 and a portion of the adjacent side wall 28. The chamber 18 is illustrated as being attached to the socket walls by threads 36. An O-ring 38 is provided to seal the chamber against escape of fluid.

Fitting in the hollow interior of the chamber 18 is a transparent collection tube 40 having a closed outer end and an open inner end. An O-ring 42 prevents fluid from the sample from flowing between the outer surface of the collection tube and the interior wall of the chamber 18. Connecting the sample-receiving chamber of the lower portion 14 of the receptacle 12 and the collection tube 40 is an opening or conduit 44 extending through the wall 28, which allows fluid from the sample to move during spinning into the collection tube. The transparent windows 22 are provided in both the upper and lower walls of the chambers 18 to enable the liquid level in the collection tubes to be observed during operation. The lower window would normally be used to allow a light source to shine into the collection tube to allow the liquid level to be more apparent when making visual observations through the top window. The collection tubes 40 and the windows 22 may be formed of any suitable glass or plastic which can withstand the stresses of operation and enable collected fluid to be visually monitored. Graduations may be marked on the windows to enable visual measurements of the fluid level to be made.

In practice, a test sample disk which has been saturated with one of the fluids involved, such as water, is simply placed in a receptacle filled with the other fluid, such as oil, and the lid is threaded into place. Even though the disk may be quite large, for example from 3"-6" in diameter, the spinning operation produces only minimal stresses in the apparatus as compared to the stresses produced in the conventional type of centrifuge because the center of the sample disk is aligned with the axis of rotation of the receptacle. The amount of expelled fluid is then measured when a state of equilibrium is reached for the various speeds tested to determine the distribution of the immiscible fluids in the sample, and the data so gathered is used to compute the capillary pressure of the fluids in the rock in question. As indicated above, to facilitate visual measurements a light source can be set up beneath the lower windows 22 to enable the liquid level to be more easily seen through the upper windows.

Because the outer surface of the test sample is spaced from the axis of rotation a distance corresponding to the radius of the disk and because the center of the disk coincides with the axis of rotation of the receptacle, the data can be mathematically differentiated more accurately than when core plugs are employed in the centrifuge mode. In the usual mode of centrifugation with core plugs, differentiation of the data is not an exact reduction procedure. But for this invention, differentiation is an exact data reduction procedure. This holds true even if the sample is not disk-shaped but is in the form of a sector of a disk, so long as the sides of the sector intersect at a point substantially coinciding with the axis of rotation of the receptacle. A detailed discussion of the reasons why the mathematical differentiation procedures made possible by the present invention are more exact than the mathematical reduction procedures of the core plug mode of centrifugation can be found in Paper 47d presented at the 1987 AIChE Annual Meeting. The paper is entitled "CAPILLARY PRESSURE: REDUCTION OF CENTRIFUGE DATA" and was authored by R. L. Christiansen and K. S. Cerise.

As previously noted, one large sample disk used in accordance with the invention can take the place of many smaller conventional core plugs in terms of the volume of rock sample from which the data is collected, permitting a large quantity of data to be collected in a relatively short time. Another advantage of the larger sample is the greater accuracy which results from the large pore volume of the sample. As noted before, whereas a standard core plug may have a pore volume of only about 3 cc, a disk measuring 3" in diameter and 1" in height may have a pore volume in the range of 20 to 30 cc. Thus a small error in measuring fluid expelled from a standard core plug sample could introduce erroneous end results because a small error in volume can comprise a significant amount compared to the total pore volume of the sample. The same small error in measuring fluid expelled from a large sample of the size permitted by the invention, however, will have very little effect on the final results because the small volume in question would be insignificant compared to the much greater total pore volume of the sample.

It should now be clear that the test method and apparatus of the present invention allow data to be collected much more rapidly in connection with the amount of fluid expelled from a saturated sample in the presence of a second fluid, where the fluids are immiscible. The use of disk-shaped samples in a spinning apparatus of the type described instead of core plugs in the usual type of centrifuge enables large samples to be easily accommodated. Because the samples can be larger, fluid volumes on a percentage basis can be more accurately measured. Further, differentiation of the data generated permits an exact mathematical reduction rather than an approximation.

Although a preferred embodiment of the invention has been described, it should now be obvious that changes to certain of the specific details of the embodiment may be made without departing from the spirit and scope of the invention as defined in the appended claims.

What is claimed is:

1. In a method for determining the distribution of immiscible fluids in a porous medium, the steps of:
preparing a sample of the porous medium, the sample having an arcuate outer extremity the curvature of which substantially corresponds to the arc of a circle;
saturating the sample with a first fluid;
submerging the saturated sample in a second fluid which is immiscible with the first fluid;
spinning the sample about an axis of rotation substantially coincident with the center of curvature of the arcuate outer extremity of the sample; and
collecting the fluid expelled from the sample.

2. A method according to claim 1, wherein the sample is in the form of a disk.

3. A method according to claim 1, wherein the sample is in the form of a sector of a disk.

4. A method according to claim 1, wherein the volume of the first fluid is measured and used in determining the capillary pressure of the immiscible fluids in the sample.

5. A method according to claim 4, wherein the first fluid is water.

6. A method according to claim 4, wherein the sample comprises rock from an oil-bearing formation.

7. A method according to claim 6, wherein one of the immiscible fluids is oil.

8. A method according to claim 6, wherein one of the immiscible fluids is gas.

9. A method according to claim 1, wherein the sample is placed into a chamber slightly larger than but of generally the same configuration as the sample, the chamber being mounted on a rotatable shaft aligned with the center of curvature of the arcuate outer extremity of the sample.

10. Apparatus for use in expelling fluid from a porous sample, comprising:
a chamber adapted to receive a porous sample having an arcuate outer extremity the curvature of which substantially corresponds to the arc of a circle;
the chamber also having an arcuate outer extremity substantially corresponding to the arc of a circle;
means connecting the chamber to a rotatable shaft mounted substantially on the center of curvature of the arcuate outer extremity of the chamber;
means for rotating the shaft, whereby the spinning of a fluid-saturated porous sample contained in the chamber will expel fluid from the sample; and
means for capturing fluid expelled from the sample.

11. Apparatus according to claim 10, wherein the chamber is cylindrical in shape and is adapted to receive a porous sample in the shape of a circular disk, the rotatable shaft being connected to the center of a face of the cylindrical chamber.

* * * * *